United States Patent
Ito

(10) Patent No.: US 6,439,538 B1
(45) Date of Patent: Aug. 27, 2002

(54) PRESSURE VARIABLE VALVE APPARATUS AND SET PRESSURE DETECTING APPARATUS OF THE VALVE APPARATUS

(75) Inventor: Takashi Ito, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/675,230

(22) Filed: Sep. 29, 2000

(30) Foreign Application Priority Data

Oct. 4, 1999 (JP) .......................................... 11-283447

(51) Int. Cl.[7] .......................... F16K 31/08; F16K 25/00; F16K 31/44
(52) U.S. Cl. .......................... 251/65; 251/176; 251/177; 251/228; 251/233; 251/234; 251/237
(58) Field of Search .................... 251/65, 176, 177, 251/179, 228, 233, 234, 237; 137/426, 524, 530, 531; 604/9, 891.1

(56) References Cited

U.S. PATENT DOCUMENTS

| | | | |
|---|---|---|---|
| 1,462,081 A | * | 7/1923 | Breeden |
| 4,387,715 A | * | 6/1983 | Hakim et al. .................... 604/9 |
| 4,595,390 A | * | 6/1986 | Hakim et al. .................... 604/9 |
| 4,608,992 A | | 9/1986 | Hakim et al. ............... 128/654 |
| 4,615,691 A | * | 10/1986 | Hakim et al. .................... 604/9 |
| 4,676,772 A | | 6/1987 | Hooven .......................... 604/9 |
| 4,772,257 A | * | 9/1988 | Hakim et al. .................... 604/9 |
| 5,643,194 A | | 7/1997 | Negre ............................. 604/8 |
| 5,928,182 A | * | 7/1999 | Kraus et al. .................... 604/9 |
| 6,050,969 A | * | 4/2000 | Kraus ............................. 604/9 |

FOREIGN PATENT DOCUMENTS

| | | |
|---|---|---|
| EP | 0421558 | 4/1991 |
| WO | 99053990 | 10/1999 |

* cited by examiner

*Primary Examiner*—William C. Doerrler
*Assistant Examiner*—David A Bonderer
(74) *Attorney, Agent, or Firm*—Adams & Wilks

(57) ABSTRACT

A pressure variable valve apparatus includes a mover constituted to be embedded in the body and movable linearly in B direction in a main body to change pressure for releasing closure of a valve flow path by a valve element, a fixed magnetic marker provided unmovably to the main body and a variable magnetic marker integrally formed with the mover. Meanwhile, a set pressure detecting apparatus includes a magnetic sensor and a supporter for supporting from outside of the body the magnetic sensor scannably in direction for moving the variable magnetic marker to provide detected output in accordance with positions of the fixed magnetic marker and the movable magnetic marker of the valve apparatus from the magnetic sensor.

20 Claims, 9 Drawing Sheets

Figs. 4

Figs. 9
Fig. 9A
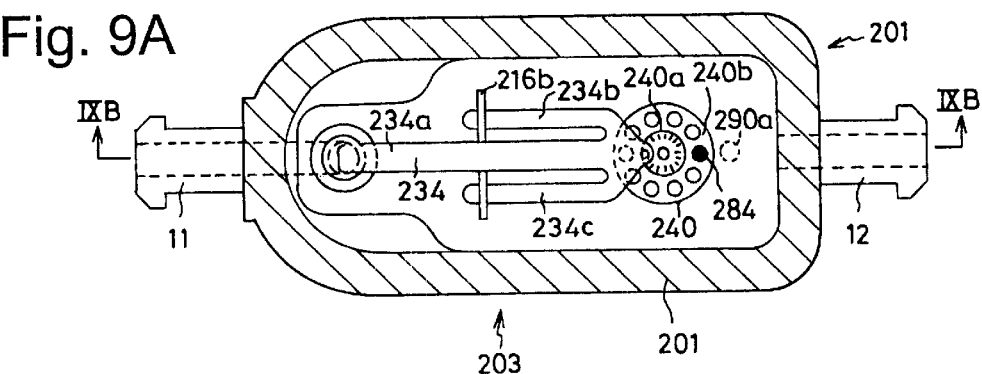
Fig. 9B
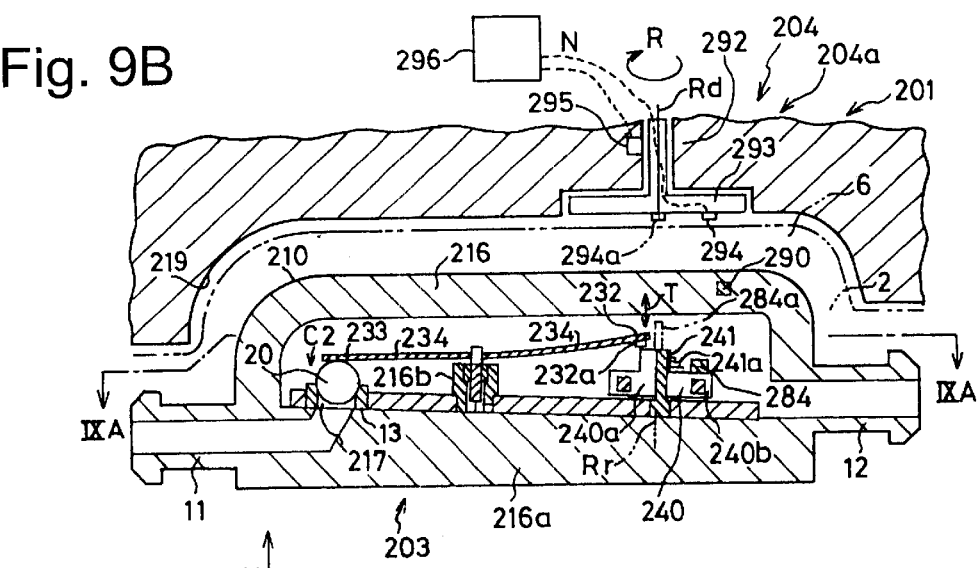
Fig. 9C
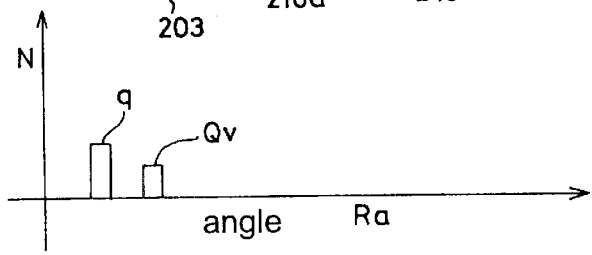

PRESSURE VARIABLE VALVE APPARATUS AND SET PRESSURE DETECTING APPARATUS OF THE VALVE APPARATUS

BACKGROUND OF THE INVENTION

1. Field of the Invention

The present invention relates to a pressure variable valve apparatus, more particularly to a pressure variable valve apparatus suitable for being used as a shunt valve embedded in the body for adjusting pressure of the cerebrospinal fluid or the like and a set pressure detecting apparatus thereof.

2. Description of the Prior Art

Japanese Patent Laid-Open No. 40063/1985 discloses a shunt valve construction in which there is provided in a flow path of the cerebrospinal fluid or the like for adjusting the pressure of the cerebrospinal fluid or the like, a shunt valve provided with a leaf-like spring one end portion of which is brought into contact with a ball serving as a valve element, the other end portion of which is engaged with a cam face in a shape of a spiral staircase integrally formed with a rotor of a multiple pole step motor element and which changes the pressing force on the ball by the spring by changing a flexing amount of the spring by moving the engaged end portion of the spring in an axial direction of the rotor in accordance with the rotation of the cam face in correspondence with rotation of the rotor for treatment of hydrocephalus or the like. A pressure variable valve apparatus of this kind is known as the "MEDOS (trademark) pressure variable type valve shunt system" and constructed such that a fixed marker referred to as white marker is provided in a main body and a movable marker is referred to as pressure indicator is provided integrally with the cam to be able to confirm the set pressure of the valve apparatus when embedded in the human body and the position of the white marker and rotational position of the pressure indicator can be detected by an X ray apparatus.

However, it is not preferable for health to irradiate the human body with X ray to thereby expose the human body to X ray every time of confirming a set pressure state of the valve apparatus.

Further, there is known in, for example, Japanese Patent Laid-Open No. 170749/1996, a valve apparatus in which one end portion of a leaf spring bent substantially in a semicircular shape is fixed to a rotor, a peripheral face of a middle portion of the leaf spring bent and extended in the semicircular shape from the fixed end portion to a free end is made to be able to be brought into contact with a valve element in a ball-like shape and press force of the ball by the spring is changed in accordance with a change in a position of bringing the spring into contact with the ball in accordance with a change in rotational angle of the rotor. The valve apparatus of this kind is known as "SOPHY valve system" and according to the valve apparatus, the rotor is formed by a permanent magnet magnetized in one diameter direction, a compass (rotatable magnetic needle) is mounted on the surface of the body at a portion embedded with the valve apparatus and the rotational angle of the permanent magnet of the rotor is detected by a direction of the magnetic needle of the compass.

However, such a constitution capable of detecting the rotational angle by such a simple means by and large, is limited to a special valve apparatus in which the set pressure can be adjusted by rotating the rotor comprising the single. (two-poled) permanent magnet in a range of angle smaller than 360 degree. According to the valve apparatus, with regard to the rotor having a magnetically simple structure comprising the two-poled permanent magnet, the rotational angle of the rotor is adjusted in the range smaller than one rotation and therefore, the constitution is not suited to the rotational position control by the step motor structure, the magnet is arranged at the surface of the body embedded with the valve apparatus and the magnet per se outside of the body is rotated to thereby directly control position of the rotor and various disadvantages are accompanied such that the rotor per se is obliged to enlarge to some degree in order to enable such position control and the like. Further, when rotational center of the compass is shifted relative to the rotational center of the rotor, there also is a concern that an indicator of the compass does not accurately represent the set pressure.

The invention has been carried out in view of the above-described points and it is an object thereof to provide a pressure variable valve apparatus capable of accurately detecting set pressure and a set pressure detecting apparatus of the valve apparatus without being injurious to health.

SUMMARY OF THE INVENTION

According to an aspect of the invention, there is provided a pressure variable valve apparatus which is a valve apparatus constituted to be embedded in the body and having a variable set pressure, the pressure variable valve apparatus comprising a movable member linearly movable in a main body to change a pressure for releasing closure of a valve flow path by a valve element, a fixed magnetic marker mounted stationally to the main body, and a movable magnetic marker integrally formed with the movable member. Meanwhile, according to another aspect of the present invention, there is provided a set pressure detecting apparatus of a pressure variable valve apparatus, the set pressure detecting apparatus comprising a magnetic sensor, and a supporter for supporting the magnetic sensor outside of the body scannably in a direction of moving the movable magnetic marker to provide from the magnetic sensor a detection output in accordance with positions of the fixed magnetic marker and the movable magnetic marker of the valve apparatus.

According to the pressure variable valve apparatus, the fixed magnetic marker indicating a reference position is mounted stationarily to the main body, the movable or moving magnetic marker is formed integrally with the movable member and accordingly, by detecting the positions of the two markers by the magnetic sensor, movement of the movable member can be detected by detecting movement of the movable magnetic marker relative to the fixed magnetic marker. Further, the movable member formed with the movable magnetic marker can be moved linearly relative to the fixed magnetic marker or the main body and accordingly, an amount of moving the movable member can be detected by detecting a distance between the two markers or an amount of changing the distance along the direction of moving the movable member. Further, the movable member is constituted to change the set pressure (pressure for releasing closure of the valve path by the valve element) by the linear movement and accordingly, by detecting the amount of moving the movable member, the set pressure of the valve apparatus can be detected. In the detecting operation, X ray irradiation or the like is not needed and there is no concern of being injurious to health.

Further, according to the set pressure detecting apparatus of the invention, the magnetic sensor is supported outside of the body by the supporter scannably in the direction of moving the movable magnetic maker to provide the detection output in accordance with the positions of the fixed magnetic marker and the variable magnetic marker of the pressure variable valve apparatus from the magnetic sensor and accordingly, the positions of the two markers can be detected firmly and accurately by the magnetic sensor. Further, in the case in which the movable member is made movable in the linear direction, so far as the valve apparatus is embedded at a site proximate to the surface of the body, the direction of moving the movable member in the valve apparatus can optically be recognized as an outer shape of the valve main body even from outside of the body and therefore, setting of the direction can be carried out easily and accurately. The linear moving direction of the movable member is typically selected to actually coincide with a direction of extending a flow path of a fluid in the body such as the cerebrospinal fluid at the portion of embedding the valve apparatus. However, when desired, the valve apparatus may be arranged slenderly in a direction intersecting with the flow path of the fluid. Further, in the case in which the movable member is provided with a plurality of the movable magnetic markers along the direction of moving the movable member, the direction may not coincide therewith excessively strictly. When magnetic fields caused by respective two magnetic poles of the permanent magnet can be detected by the magnetic sensor, the two magnet poles of the single permanent magnet are included in "plurality of the movable magnetic markers".

A scanning direction of the magnetic sensor may typically be only a direction along the direction of moving the movable member. However, depending on cases, a total of face area may be scanned by scanning the magnetic sensor in the direction of moving the movable member, that is, the longitudinal direction while carrying out line scan in a direction intersecting with the direction of moving the movable member, that is, the transverse direction over a predetermined width.

That is, in order to achieve the above-described object, the set pressure detecting apparatus according to the invention may be provided with the supporter for supporting the magnetic sensor scannably in the direction of moving the movable magnetic marker outside of the body to provide the detection output in accordance with the positions of the fixed magnetic marker and the movable magnetic marker or may be provided with the supporter for supporting the magnetic sensor outside of the body position-scannably to provide the detection output in accordance with the positions of the fixed magnetic marker and the movable magnetic marker from the magnetic sensor.

The magnetic marker may detect the position in combination with the magnetic sensor. Typically, the magnetic marker comprises a permanent magnet and the magnetic sensor detects the position of the magnetic marker by detecting intensity or direction of a magnetic field formed by the permanent magnet. The magnetic sensor for detecting the intensity of the magnetic field is typically constituted by a static magnetic field detector such as a magnetoresistive element, a Hall element, a magnetic impedance element or the like. The magnetoresistive element may be so-to-speak AMR element utilizing anisotropic magnetoresistive effect or so-to-speak GMR element utilizing gigantic magnetoresistive effect. In the case of AMR element, the AMR element may be of a type increasing electric resistance by magnetic field or may be of a type of reducing thereof and causing negative magnetoresistive effect. Further, a plurality of magnetoresistive elements may be combined to promote the sensitivity of the magnetic sensor. Further, in the case in which the magnetic sensor is moved at constant speed (scan at constant speed) the magnetic sensor may be a pickup coil for detecting a variation in the magnetic field. Further, depending on cases, the magnetic sensor may be constituted by an electromagnet power of which is fed by outside power source and the magnetic marker may be constituted by any other system of detecting a variation in the magnetic state such as a ferromagnetic member having high permeability capable of providing a variation in a magnetic circuit formed by the electromagnet.

The fixed magnetic marker is mounted stationally to the main body such that the fixed magnetic marker stays unmoved relative to the main body and is typically embedded at a portion of the main body proximate to the surface of the body. However, depending on cases, the fixed magnetic marker may be provided at a portion of the main body remote from the surface of the body. The fixed magnetic marker may be provided normally at a portion referred to by a name other than the main body or the valve housing so far as the fixed magnetic marker is mounted stationally to the main body and stays unmoved relative to the main body.

The movable magnetic marker can differ depending on way of forming a linearly moved movable member. That is, the movable member may be constituted by a mover of a linearly driven step motor element or may be coupled to a conversion mechanism for converting rotation of a rotor of a rotary type step motor element into linear motion and moved linearly.

In the case of the former, typically the mover is provided with a mover main body comprising a permanent magnet and the movable magnetic marker comprises the permanent magnet of the mover main body. However, when desired, a soft magnetic member such as permalloy material or the like may separately be provided to the mover as the movable magnetic marker. In the case of the latter, the movable magnetic marker is typically constructed by a constitution similar to the fixed magnetic marker.

The structure of the supporter of the magnetic sensor of the set pressure detecting apparatus may be constituted in any way so far as the supporter can be arranged by aligning its direction in the direction of moving the movable member of the valve apparatus at a position covering the valve apparatus embedded in the body and the magnetic sensor can be supported proximate to the surface of the body movably in the direction of moving the movable member.

Further, in order to achieve the above-described object, according to another aspect of the invention, there is provided a pressure variable valve apparatus which is a valve apparatus constituted to be embedded in the body and having a variable set pressure, the pressure variable valve apparatus comprising a rotor of a rotary type step motor element comprising a multiple poles permanent magnet structure, a rotational position of said rotor being adjustable to change a pressure for releasing closure of a valve flow path by a valve element, a fixed magnetic marker mounted stationary to a main body, and a movable magnetic marker integrally formed with the rotor.

According to the valve apparatus, the pressure of releasing closure of the valve flow path by the valve element is set and adjusted by the rotor of the rotary type step motor element comprising the multiple poles permanent magnet structure and capable of adjusting the rotational position and accordingly, the set pressure can finely be controlled without excessively enlarging the stator structure. The valve apparatus according to this aspect has an advantage substantially similar to the valve apparatus according to the above-described aspect except that the movable magnetic marker is provided to the rotor. Further, in this case, the rotor comprises the multiple poles permanent magnet structure and therefore, the rotational state cannot actually be specified by a compass (magnetic needle), however, by attaching the movable magnetic marker to the rotor, the rotational state of the rotor can be detected by detecting the position of the movable marker. Here, the "multiple poles" permanent magnet structure is referred to as a constitution in which at least two permanent magnets are combined.

In the above-described, each of the fixed magnetic marker and the movable magnetic marker is typically constituted by one or one location of magnetic marker. However, when desired, by providing two, that is, two locations of the fixed magnetic marker or the movable magnetic marker, the direction of the main body may be specified or by providing three or three locations thereof, the position of the rotational center of the rotor may be specified. Further, instead of detecting or evaluating arrangement of the fixed magnetic marker by a relative position in a state in which the arrangement is projected to a two-dimensional plane in parallel with the surface of the body, for example, by detecting or evaluating also the magnitude of the detection signal of the magnetic marker (that is, intensity of magnetic field) as the detection output of the magnetic sensor, a direction of arranging the valve apparatus, for example, an inclined state relative to the surface of the body may be specified.

Further, the another aspect of the set pressure detecting apparatus of the pressure variable valve apparatus is constituted similar to the above-described aspect of the set pressure detecting apparatus of the pressure variable valve apparatus except that the direction of moving the magnetic sensor differs in correspondence with the direction of moving the variable magnetic marker.

The valve apparatus of a type having the movable member movable in the linear direction to change the set pressure, is provided with, for example, a long-sized elastic member typically comprising a leaf spring, a base end portion of which is fixed and a front end portion of which is brought into contact with a valve element in a mode of a ball or the like and a movable member movable actually linearly along a longitudinal direction of the elastic member between both end portions of the elastic member and having a fulcrum portion for flexing the elastic member between the both end portions of the elastic member. The fulcrum portion may be a protruded portion or a projected portion formed at a position of the movable member opposed to one surface of the elastic member or may be a rolling member such as a ball or a roller contained and supported rollably by a main body portion of the movable member. A front end of the protruded portion or the projected portion, which presses the surface by being brought into contact with the surface of the elastic member, may be formed in a dot-like shape or in a linear shape extended in a direction intersecting with the longitudinal direction of the elastic member, typically, in a direction orthogonal thereto.

The above-described valve apparatus is used by, for example, in combination with a movable member position control apparatus applying an actually uniform pulse-like magnetic field directed in a direction actually orthogonal to the longitudinal direction of the elastic member over an entire length of the movable member in the moving direction to move the movable member in the longitudinal direction of the spring.

Meanwhile, according to a valve apparatus of a type for changing pressure of releasing closure of a valve flow path by a valve element by adjusting a rotational position of a rotor of a rotary type step motor element comprising a multiple poles permanent magnetic structure, for example, as disclosed in Japanese Patent Laid-Open No. 40063/1985, mentioned above, there is provided the spring in the plate-like shape, one end portion of which is brought into contact with the ball serving as the valve member, other end portion of the spring is engaged with the cam face in the shape of the spiral staircase formed integrally with the rotor of the mode of the multiple poles permanent magnet structure and the amount of flexing the spring is changed by moving the engaged end portion of the spring in the axial direction of the rotor in accordance with rotation of the cam face accompanied by rotation of the rotor to thereby change the press force exerted to the ball by the spring.

The valve apparatus is constituted to be used by being embedded in the human body for the medical use or the like and is typically constituted such that the valve apparatus can surgically be embedded in the body to be used as, for example, a shunt valve for the ventricle of the brain—the abdominal cavity shunt or the ventricle of the brain—the ventricle of the heart such that pressure of related fluid in the body can noninvasively be adjusted with a purpose of treatment of hydrocephalus, cerebral tumor, subarachnoid cyst or the like and the valve apparatus can be provided with a size of about several cm or smaller suitable for being used for adjusting pressure of the cerebrospinal fluid or the like.

BRIEF DESCRIPTION OF THE DRAWINGS

A preferred form of the present invention is illustrated in the accompanying drawings in which:

FIG. 4 are for explaining detection of set pressure by a set pressure detecting device of the valve system of FIG. 1 in which

7A shows a section similar to that in FIG. 1 in a state before applying the system to the human body and is an explanatory view of a section taken along a line VIIA—VIIA of FIG. 8 and FIG. 7B is an explanatory view similar to FIG. 4B with regard to the detection output of a magnetic sensor.

FIG. 9 show a valve system of still other preferable embodiment according to the invention in which FIG. 9A is an explanatory view of a section taken along a line IXA—IXA of FIG. 9B and FIG. 9B is an explanatory view of a section taken along a line IXB—IXB of FIG. 9A and FIG. 9C is a schematic graph showing an example of detection output.

DETAILED DESCRIPTION OF THE PREFERRED EMBODIMENTS

Next, an explanation will be given of several preferable modes of carrying out the invention based on embodiments shown in the attached drawings.

Figure 1:
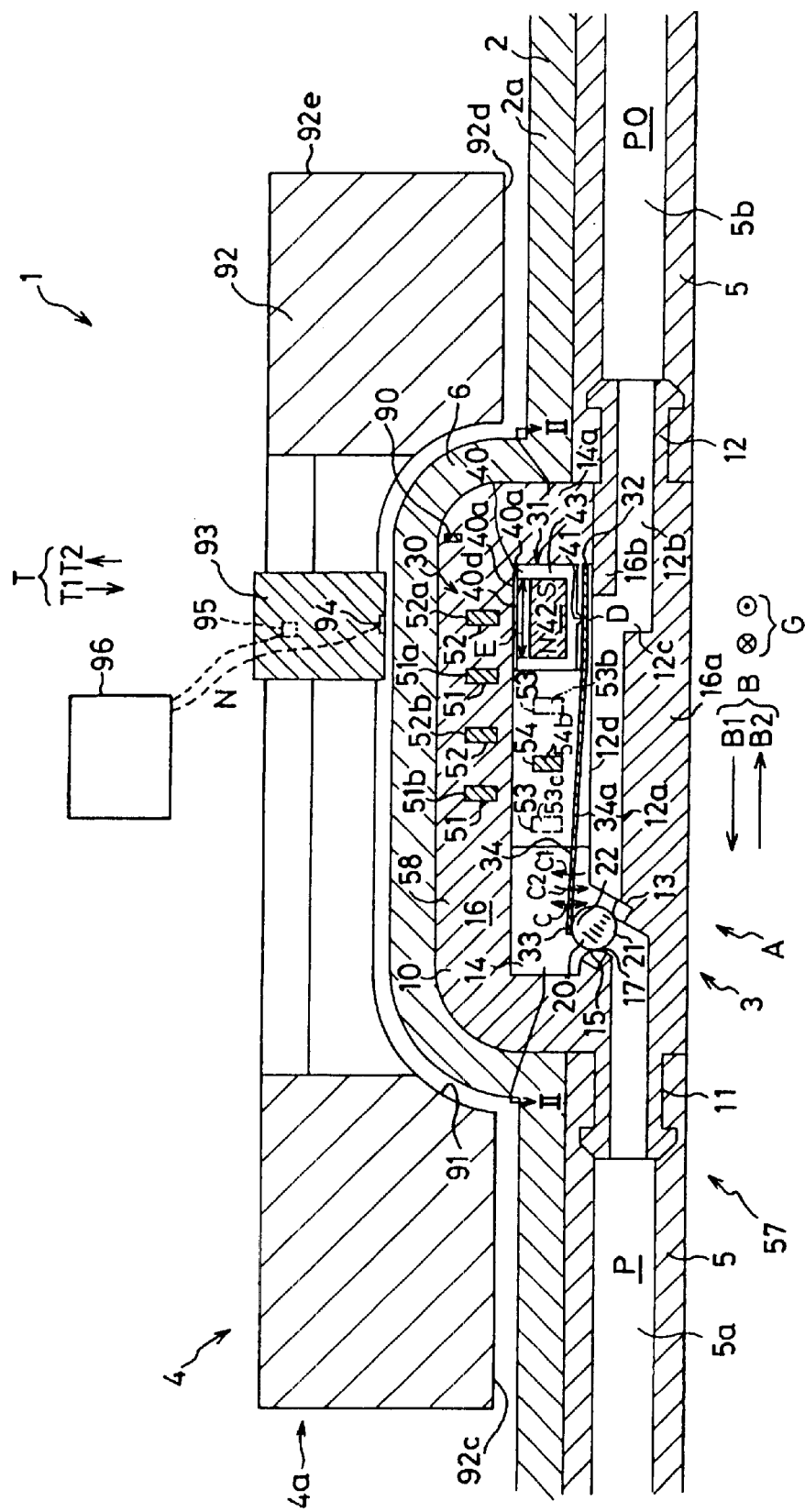
FIG. 1 shows a valve system of a preferable embodiment according to the invention applied to the human body and is an explanatory view of a section taken along a line I—I of FIG. 2 (however, stator pole pieces on this side are shown by imaginary lines)
Figure 2:
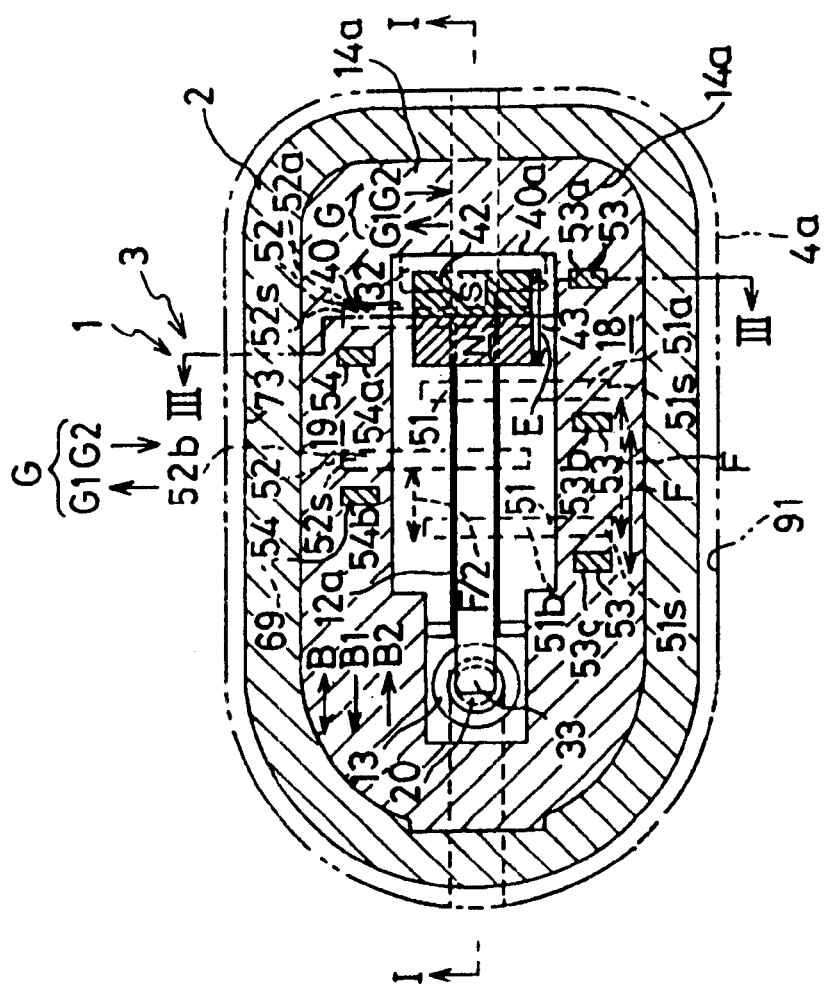
FIG. 2 is an explanatory view of a section taken along a line II—II of the valve system of FIG. 1 (however, with regard to a set pressure detecting device, only an edge of a recess portion is shown by imaginary lines)
Figure 3:
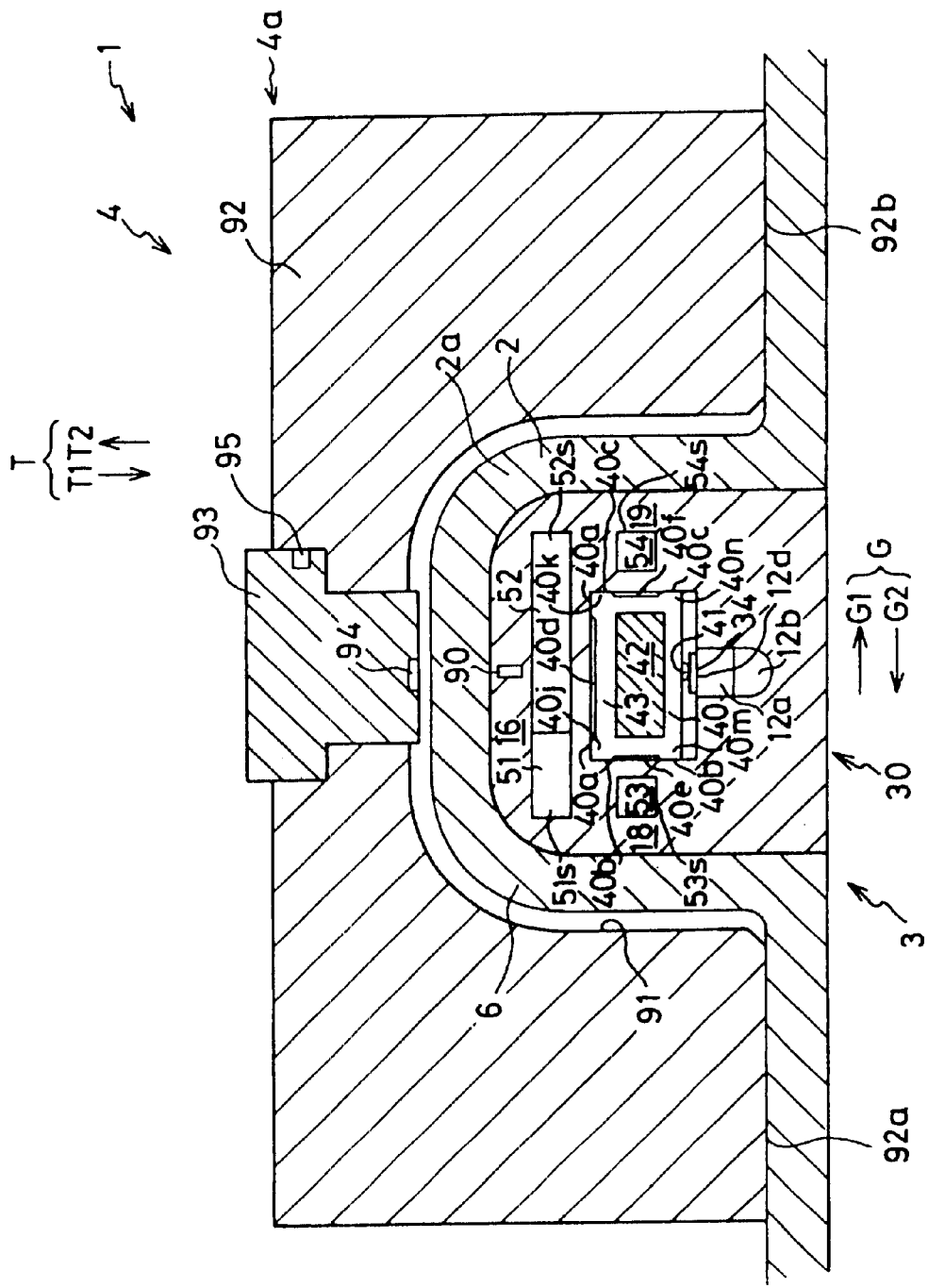
FIG. 3 is an explanatory view of a section taken along a line III—III of FIG. 2 with regard to the valve system of FIG. 1.

First, FIGS. 1 through 3 show a valve system 1 of a first embodiment in a state in which the valve system 1 is applied to the human body for simply clarifying the explanation.

A valve system 1 is constituted by a pressure variable valve apparatus 3 embedded in the human body 2 and a pressure detecting and controlling apparatus 4 and the pressure detecting and controlling apparatus 4 includes a pressure detecting device 4a for detecting set pressure ΔP of the valve apparatus 3 and a pressure controlling device 4b for adjusting or controlling the set pressure ΔP.

The valve apparatus 3 is connected and arranged at, for example, a portion A at a middle of a conduit 5 of the cerebrospinal fluid for setting and adjusting pressure P of the cerebrospinal fluid at an upstream conduit portion 5a such that the pressure P does not become higher than pressure P0 of the cerebrospinal fluid at a downstream side conduit portion 5b by set pressure ΔP of the valve apparatus 3 or higher. That is, the pressure P of the cerebrospinal fluid is set and adjusted to be equal or lower than P0+ΔP. For example, in the case in which the pressure P0 actually coincides with the atmospheric pressure, when P0=0 with the atmospheric pressure as a reference, P=ΔP. Further, the valve apparatus 3 may be used as a valve apparatus for adjusting pressure such that the pressure of the downstream side conduit portion 5b becomes equal to or higher than predetermined pressure P0 (=P−ΔP).

The valve apparatus 3 is provided with an entry side and an outlet side conduit portion 11 and 12, a chamber 14 communicating with the outlet side conduit portion 12 and an opening 17 as a valve flow path for connecting the entry side conduit portion 11, the outlet side conduit portion 12 and the chamber 14 at inside thereof and is provided with a main body or a valve housing 10 comprising silicone resin, polycarbonate or the like, a valve member or a valve element 20 in a shape of a ball made of hard ceramic such as sapphire, ruby or the like for opening and closing the opening 17 in the main body 10 and a pressure adjusting mechanism 30 for releasing closure of the flow path 17 by the ball valve 20 in cooperation with the ball valve 20 when the pressure P of the upstream side conduit 5a exceeds the set pressure P0+ΔP. According to the valve housing 10, for example, the width is about several mm through 2 cm, the length is about several mm through 5 cm and the height is about several mm through 1 cm. However, sizes in the respective directions may be smaller or larger depending on cases.

More in details, the main body 10 is provided with the inlet side conduit portion 11 connected to the upstream side conduit portion 5a, the outlet side conduit portion 12 connected to the downstream side conduit portion 5b, a valve seat portion 13 on which the ball valve 20 can be seated between the inlet side and the outlet side conduit portions 11 and 12 and which comprises a material similar to that of the ball 20 and the chamber 14 containing the ball valve 20 and a main body portion 31 of the pressure adjusting mechanism 30. The outlet side conduit portion 12 is provided with a first conduit portion 12a disposed just downstream from the ball valve 20, a second conduit portion 12b communicating with the downstream side cerebrospinal fluid conduit portion 5b and a connection tube portion 12c extended in the up and down direction T in FIG. 2 between the first and the second conduit portions 12a and 12b and the first conduit portion 12a and the connection tube portion 12 comprise a groove formed at a bottom wall 16a of the chamber 14. The valve seat portion 13 comprises a valve seat member having a seat face 15 in a shape of a fulcrum of a circular cone.

The main body portion 31 of the pressure adjusting mechanism 30 is provided with a leaf spring 34 in a flat plate shape one end 32 of which is fixed to the main body 10 and other end 33 of which is extended from the end portion 32 in B direction and is brought into contact with the ball 20 and a fulcrum position changing member or movable member 40 for pressing and flexing the leaf spring 34 by a fulcrum projection 41 at a middle portion of the spring 34 between the doubly supported end portions 32 and 33 to change a flexing state of the leaf spring 34 in C direction. The spring 34 comprises a nonmagnetic metal material such as, for example, nonmagnetic stainless steel, the width is about 1 mm, the thickness is about 0.1 mm and the length is about 1 through 2c m. However, sizes in the respective directions may be smaller or larger depending on cases. As shown by FIG. 3, the movable member 40 is provided with recess portions 40d, 40e and 40f permitting to pass the physical fluid such as the cerebrospinal fluid at central portions of a top face 40a and both side faces 40b and 40c and can move forward and move backward in B1 and B2 directions (summarizingly referred to by notation B) in a state in which the faces 40a, 40b and 40c constituting four corners 40j, 40k, 40m and 40n, are brought into sliding contact with a top wall 16 and both side walls 18 and 19 of the chamber 14 except that a bottom face 40h is supported by the spring 34 at the projection 41. Further, a ball bearing made of ceramic may be provided between the movable member 40 and the main body 10 and the movable member 40 may be made rollable relative to the main body 10 at the bearing ball portion. Although in FIG. 3, the fulcrum projection 41 is shown as a projected streak extended in G direction, the fulcrum projection 41 may be in a dot-like shape or a rolling object like a ball, also in G direction. Further, G direction and B direction are directions orthogonal to each other and disposed on a horizontal face in the state shown by FIGS. 1 through 3. Although in the following explanation, with apparent directions of FIGS. 1 through 3 as the bases, technical terms of horizontal direction and up and down direction are used, it is apparent that these directions can be varied depending on directions of the human body 2 embedded with the valve apparatus 3.

The spring 34 exerts press force to the ball 20 in a direction C2 of closing the opening 17 between the peripheral face of the ball 20 and the valve seat face 15 at a portion 22 of the ball 20 on a side actually opposed to a portion 21 in contact with the valve seat 13. Typically, the spring 34 is only fixed to an upper side wall 16b of the conduit 12b constituting an upper bottom wall of the chamber 14 of the main body 10 at the base end portion 32 (FIG. 2) having a width in G direction substantially the same as that of the movable member 40 and is not brought into contact with the bottom walls 16a and 16b of the chamber 14 but separated from the wall portions 16a and 16b at a middle portion shifted from the end portion 32 in B1 direction. As is apparent from FIGS. 1 and 3, in this example, the partition wall 16b for separating the chamber 14 from the conduit 12a is not present at the conduit portion 12a and the connection tube portion 12c, an upper side end of the conduit 12a is exposed to the chamber 14 at an opening 12d and the width of the spring 34 (length in G direction) is slightly smaller than the width of the conduit portion 12a. Therefore, the spring 34 is doubly supported by the end portions 32 and 33 and is pressed at a portion D by the fulcrum projection 41. However, when desired, the partition wall 16b constituting a top wall of the conduit portion 12a may be formed at a total of the chamber 14. However, in that case, it is preferable that a gap remains between the partition wall 16a and the spring 34 in a region between the fulcrum position D and the fixed base end portion 32 to avoid stress from being concentrated excessively at the fulcrum position D pressed by the fulcrum 41 of the movable member 40. Further, it is preferable that the gap is comparatively large to avoid the physical fluid in the chamber 14 from staying in the gap.

The movable member 40 is constituted by embedding a permanent magnet 42 having a length E (for example, about 2 through 3 mm) magnetized in B1 direction in a movable housing 43 as a movable member main body comprising silicone resin, polycarbonate or the like and the fulcrum projection 41 is formed at a bottom portion of the housing 43. The permanent magnet 42 comprising a hard magnetic material such as Sm—Co series alloy may be constituted by a single member or may be constituted by laminating a plurality of magnets in the same magnetizing direction as shown by FIG. 2 and direction of magnetization of the magnet 42 maybe in B2 direction reverse to the illustrated.

The top wall 16 and the both side walls 18 and 19 of the main body 10, are embedded with a plurality or a number of two sets and four groups of stator pole pieces 51, 52 and 53, 54 each comprising a soft magnetic member such as permalloy having high permeability at predetermined intervals F in B direction. Here, a technical term of ferromagnetism is in a broad sense including ferrimagnetism or the like.

More in details, the stator pole pieces 51 embedded in the top wall 16 at intervals F, are extended from a vicinity of surface of the side wall 18 in G direction orthogonal to B direction actually over an entire width of the permanent magnet 42. It is preferable that respective end portions of the stator pole piece 51 disposed at vicinities of the surface of the housing 43 are extended to locations as proximate to the surface as possible so far as the seal state of the chamber 14 and the conduit portion 12 can be maintained firmly (same goes with also other stator pole piece, mentioned later). FIG. 2 shows two of such stator pole pieces 51 by notations 51a and 51b. Similarly, the stator pole pieces 52 embedded in the top wall 16 at the interval F are extended from vicinities of surface of the side wall 19 in G direction orthogonal to B direction and extended substantially over the total width of the permanent magnet 42. FIG. 2 shows two of such stator pole pieces 52 by notations 52a and 52b. The stator pole pieces 51a, 52a, 51b and 52b are disposed equally at intervals E=F/2 actually coinciding with the distance or the length E between magnetic poles of the magnet 42. That is, the stator pole piece 51a is disposed just at middle of the stator pole pieces 52a and 52b in B direction, the stator pole piece 52b is disposed just at middle of the stator pole pieces 51a and 51b and the distance between the stator pole pieces 51 and 52 in B direction which are contiguous in B direction, actually coincides with the length E=F/2 of the permanent magnet 42 of the mover 40.

Similarly, the stator pole pieces 53 embedded in the side wall 18 at intervals F in B direction, are extended in G direction from a vicinity of an outer surface of the side wall 18 to a vicinity of an inner surface thereof. FIG. 2 shows three of such stator pole pieces 53 by notations 53a, 53b and 53c. Further, the stator pole pieces 54 embedded in the side wall 19 at intervals F are extended in G direction from a vicinity of an outer surface of the side wall 19 to a vicinity of an inner surface thereof. FIG. 2 shows two of such stator pole pieces 54 by notations 54a and 54b. The stator pole pieces 53a, 54a, 53b, 54b and 53c are also disposed at equal intervals by the interval E=F/2 actually coinciding with the distance or the length E between the magnetic poles of the magnet 42, the stator pole piece 53b is disposed just at middle of the stator pole pieces 54a and 54b, the stator pole picas 54a is disposed just at middle of the stator pole pieces 53a and 53b and the stator pole piece 54b is disposed just at middle of the stator pole pieces 53b and 53c and the distance in B direction between the stator pole pieces 53 and 54 which are contiguous in B direction, actually coincides with the length E=F/2 of the permanent magnet 42 of the mover 40.

Further, intervals among the stator pole pieces 53a, 52a, 54a, 51a, 53b, 52b, 54b, 51b and 53c which are mostly contiguous in B direction, are the same and E/2. Further, according to the mover 40 having the permanent magnet 42, in an initial state in which the end face 40a in B2 direction is brought into contact with a side wall 14a of the chamber 14, S pole of the magnet 42 is disposed at a position mostly proximate to the stator pole piece 53a, N pole is disposed at a position mostly proximate to the stator pole piece 54a and at the positions, a magnetic path for magnetizing the stator pole pieces 53a and 54a is formed, the permanent magnet 42 is brought into a state of being attracted to the two stator pole pieces 53a and 54a and there is exerted hold force for holding the mover 40 at the positions. At this occasion, the stator pole piece 52a is disposed just at center of the two magnetic poles of the permanent magnet 42 and almost no force is exerted actually between the stator pole piece 52a and the permanent magnet 42. Further, a distance between the other stator pole piece and the permanent magnet 42 is comparatively large and therefore, a force by the other stator pole piece exerted on the mover 40 via the permanent magnet 42, is actually negligible in comparison with the force exerted by the stator pole pieces 53a and 54a on the mover 40. Such a position of holding the mover 40 is realized similarly at each pitch of E/2 in B direction from the initial position by similar reason and accordingly, even in a state in which the stator pole piece is not magnetized from outside, the mover 40 is provided with stable hold positions at pitch of E/2.

Further, in changing a number of the hold positions, a number of the respective stator pole pieces 51, 52, 53 and 54 may be changed and in changing intervals among the hold positions, the length E in B direction of the magnet 42 and the interval E/2 between the contiguous stator pole pieces may be changed. A stator 58 for forming a linear step motor element 57 in cooperation with the mover 40, comprises the stator pole pieces 51, 52, 53 and 54 embedded in the wall portions 16, 18 and 19 of the housing 10.

The pressure variable valve apparatus 3 is provided with a fixed magnetic marker 90 embedded in the top wall 16 at a central portion in G direction of the top wall 16 of the main body 10 and at a vicinity of an end portion thereof in B2 direction. The fixed magnetic marker 90 is constituted by, for example, a permanent magnet piece and the permanent magnet piece is magnetized in, for example, a direction orthogonal to the top wall 16. Although the fixed magnetic marker 90 is preferably provided at a position as remote as possible from the stator to minimize influence of magnetization of the marker 90 effected on magnetized states of the stator pole pieces 52 and 51 or the like, since only static magnetic field is effected on the stator pole pieces, the static magnetic marker 90 maybe provided as proximate to the stator poles as possible when operation of the system 1 is not actually influenced thereby. Further, according to the valve apparatus 3, a movable magnetic marker comprises the permanent magnet 42 of the mover 40, more particularly, two magnetic poles N and S of the magnet 42.

Therefore, as is apparent from FIG. 3, the fixed magnetic marker 90 and the movable magnetic marker 42 are at positions overlapped in the up and down direction in view of positions in G direction. Meanwhile, in view of position in B direction, the position of the movable magnetic marker 42 relative to that of the fixed magnetic marker 90 is changed by change of position of the mover 40 in B direction.

Meanwhile, as is apparent from FIGS. 1 through 3, the pressure detecting device 4a for detecting the set pressure AEP of the pressure variable valve apparatus 3, includes a detecting device main body 92 having a recess portion 91 in a slender shape substantially complementary to an eminence portion 6 of the scalp or the like having a contour shape substantially coinciding with a contour shape of the main body 10 at the head portion embedded with the value apparatus 3, a detector slider 92 slidably supported in B1 or B2 direction relative to the main body 92 when the detecting device main body 92 is arranged at a predetermined position shown by FIGS. 1 through 3, and a magnetic sensor 94 such as a magnetoresistive element mounted to a bottom portion of the slider 93. Although not illustrated for simply clarifying the explanation, when a sensor main body portion for detecting intensity of a magnetic field in, for example, T1 direction (lower direction) in the magnetic sensor 94, is constituted by a magnetoresistive element such as AMR, GMR or MI element, a hall element, a magnetic impedance element or the like, the sensor main body is arranged at the illustrated position designated by notation 94 and related power source or circuit are provided in the detecting device main body 92 or outside of the main body 92 separately. A magnetic field component detected by the sensor may be inclined in a desired specific direction relative to the up and down direction T. When the direction detecting device main body 92 is arranged at the illustrated predetermined position, for example, the recess portion 91 is fitted just to the eminence portion 6 on both sides of the eminence portion 6 in G direction, and bottom faces 92a and 92b are brought into close contact with the surface of the skin 2 on the both sides of the eminence portion 6 (FIG. 3). Further, although according to the example shown in FIG. 1, bottom faces 92c and 92d are separated from the surface of the skin 2 on the both sides in B direction, if possible, it is preferable that the bottom faces 92c and 92d are also brought into close contact with the surface of the skin 2. However, although the contour of the human body at a surrounding of a portion of embedding the valve 3 is not constant and can be complicated and therefore, the state of FIG. 1 exemplifies that there is also a case in which the optimum condition is not necessarily satisfied. Further, the pressure detecting device 4a is further provided with a slide position detector 95 for detecting a predetermined position of the detecting device main body 92, for example, a B direction position Xb of the magnetic sensor 94 with B1 direction end portion 92e as a reference and a display portion 96 for displaying detection output n of the magnetic sensor 94. Further, although in this case, the position of the end portion 92e is defined as the reference position for convenience in the case in which the surface of the skin is marked for easy to see the reference position of the surface of the skin of the human body 2 even when the main body 92 of the detecting device 4a has been removed, the reference position of the position Xb in B direction may be other arbitrary position.

In the following, it seems that although the detector output N detects, for example, a magnetic field in accordance with magnetized states of the stator pole pieces 51 and 52 embedded in the top wall 16, the detector is moved in B direction at positions where a change in the magnetic field accompanied by the variation in magnetized states of the stator pole pieces 53 and 54 embedded in the side walls 18 and 19 cannot be detected. Further, although illustrated enlargedly for easy to see in FIG. 1, a distance between the sensor 94 and the mover 40 in the up and down direction T is, for example, about 1 through 3 mm or smaller and is extremely small.

Figure 4A:
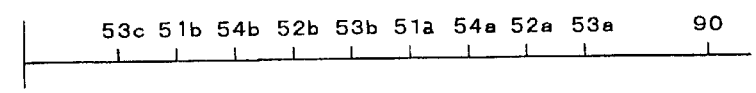
FIG. 4A is an explanatory view showing a position of a fixed magnetic marker and positions of stator pole pieces related to positions of magnetic poles of a permanent magnet of a mover constituting a movable magnetic marker.
Figure 4B:
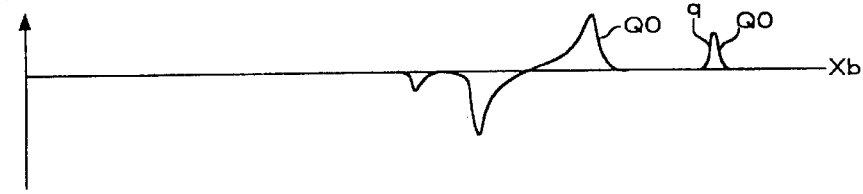
FIG. 4B is a schematic graph showing a pattern of detection output when the mover is at an initial position.

When the mover 40 is at an initial position as shown by FIGS. 1 through 3, the stator pole piece 52a is disposed at middle of the magnetic poles of the permanent magnet 42 of the mover 40 and is not magnetized at all thereby, the stator pole piece 51a comparatively proximate to N pole of the permanent magnet 42 is magnetized to some degree and accordingly, the detector output N is varied in pattern Q0 as shown by, for example, bold lines in FIG. 4B. Although in this case, an explanation has been given of an example of a type in which electric resistance is increased or reduced in accordance with direction of magnetic field as in GMR element, there may be used a magnetic sensor of a type depending actually on only magnitude of magnetic field in T direction and not in direction T1 or T2 as in AMR element and in that case, a peak pattern shown below the axis Xb is provided with a shape which is inverted relative to the Xb axis.

Figure 4C:
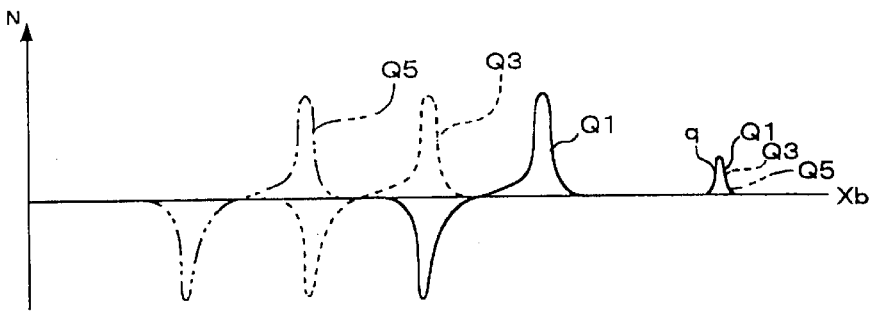
FIG. 4C is a schematic graph showing a pattern of the detection output when the mover is moved from the initial position by odd number steps and FIG. 4D is a schematic graph showing a pattern of the detection output when the mover is moved from the initial position by even number steps.

Meanwhile, when the mover 40 and the permanent magnet 42 are moved by 1 step in B1 direction, an S pole is disposed just below the stator pole piece 52a and an N pole is disposed just below the stator piece 51a, the respective stator pole pieces 52a and 51a are magnetized in reverse directions in view of the up and down direction T. Meanwhile, the other stator pole pieces in the top wall 16 are not magnetized. Therefore, the detector output N is varied by for example, the pattern Q1 as shown by bold lines in FIG. 4C in accordance with the position Xb of the detector 94 accompanied by sliding movement of the detector slider 93 in the B1 direction.

Figure 4D:
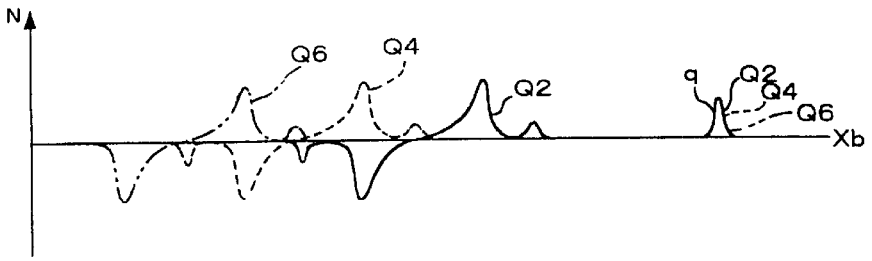

When the mover 40 and permanent magnet 42 are moved further by 1 step in B1 direction, the stator pole piece 51a is disposed at middle of the magnetic poles N and S of the permanent magnet 42 of the mover 40 and is not magnetized at all, the stator pole pieces 52a and 52b comparatively proximate respectively to S pole and N pole of the permanent magnet 42 are magnetized to some degree and therefore, the detector output N is varied in, for example, pattern Q2 as shown by bold lines of FIG. 4D in accordance with the position Xb of the detector 94 accompanied by sliding movement of the detector slider 93 in B1 direction.

Similarly, in accordance with the position of the mover 40, except a portion "q" where a magnetic field caused by the fixed magnetic marker 90 is detected, output of the magnetic sensor 94 is varied in pattern Q3 (broken lines in FIG. 4C) where the patterns Q1 and Q2 are moved by 2 steps or 4 steps respectively, Q4 (broken lines of FIG. 4D) or Q5 (two-dotted chain lines of FIG. 4C) or Q6 (two-dotted chain lines of FIG. 4D).

In the case in which the set pressure ΔP of the valve apparatus 3 is not accurately known, when the detector slider 93 is moved in B direction relative to the detector main body 92 in the set pressure detecting device 4a, in accordance with the B direction position of the mover 40, any of these patterns Q0 through Q6 (summarizingly referred to by notation "Q"), is displayed on the display 96 with the abscissa as output of the sensor position detector 95 and with the ordinate as the magnetic sensor output N.

Accordingly, by calculating a difference (distance) or a deviation between a position of the peak at the detected output pattern portion "q" of the fixed magnetic marker 90 and a position of a large peak of the pattern Q, the B direction position of the mover 40, in other words, the set pressure ΔP of the valve 3 can be detected. In detecting the set pressure ΔP, it is not necessary to expose the human body to what may be injurious for the health as in X ray. Further, in detecting the deviation between the peaks, accuracy of interval E/2 in B direction of the stator pole pieces is sufficient and therefore, it is not necessary to strictly detect positions of the respective peaks. Further, when the fixed magnetic marker 90 is provided with a length in G direction to some degree, with regard to the respective patterns Q, even when the longitudinal direction of the detecting device main body 92 is deviated (inclined) relative to the moving direction B of the mover 40 in the valve apparatus 3, a ratio of a distance between two large peaks directed reversely caused by the magnetic poles N and S of the permanent magnet 42 of the mover 40 (that is, two movable magnetic markers), versus, a distance between peaks caused by a magnetic pole at an end in B2 direction (in this example, magnetic pole S) and the fixed magnetic marker 90, stays constant and therefore, it is not necessary to strictly coincide the direction of the detecting device main body 92 (longitudinal direction) with the direction of the main body 10 of the valve apparatus 3.

Although according to the example, the fixed magnetic marker 90 is provided at the central portion in the width direction of the topwall 16 of the main body 10 such that magnetic field variation can be detected firmly and easily by one time linear B direction movement or scanning of the magnetic sensor 94, the fixed magnetic marker 90 may be provided at other position such as, for example, the side wall 18 or 19 so far as the fixed magnetic marker 90 is fixed or stationally mounted to the apparatus main body at a position which can be detected by the magnetic sensor 94.

Figure 5:
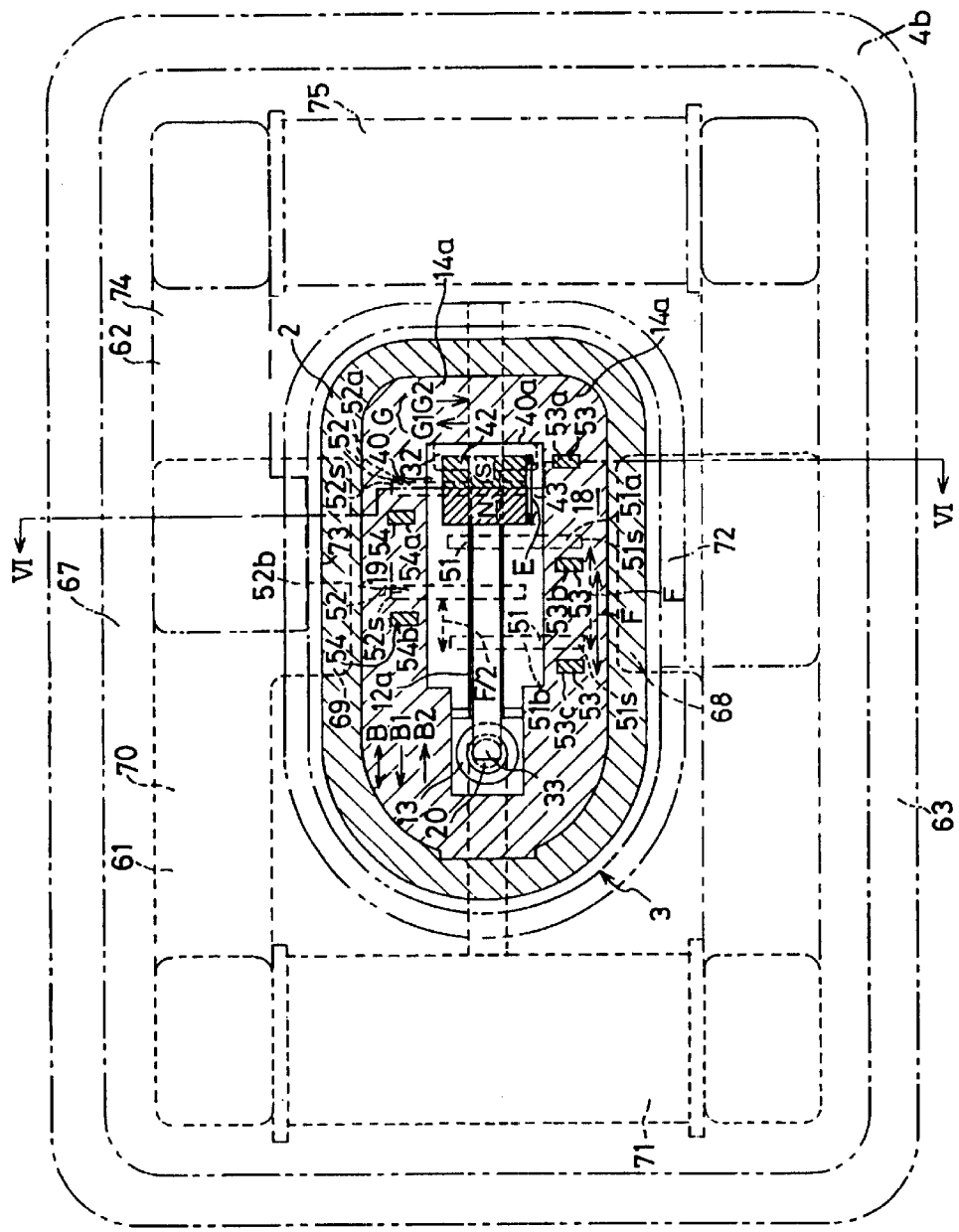
FIG. 5 shows a state in which a set pressure controlling device is applied to the valve apparatus of FIG. 1 and is an explanatory view of a section taken along a line V—V of a valve system of FIG. 6 (however, stator pole pieces disposed above are shown by broken lines, related electromagnets are similarly shown by broken lines and other portions of the control apparatus are added by imaginary lines).
Figure 6:
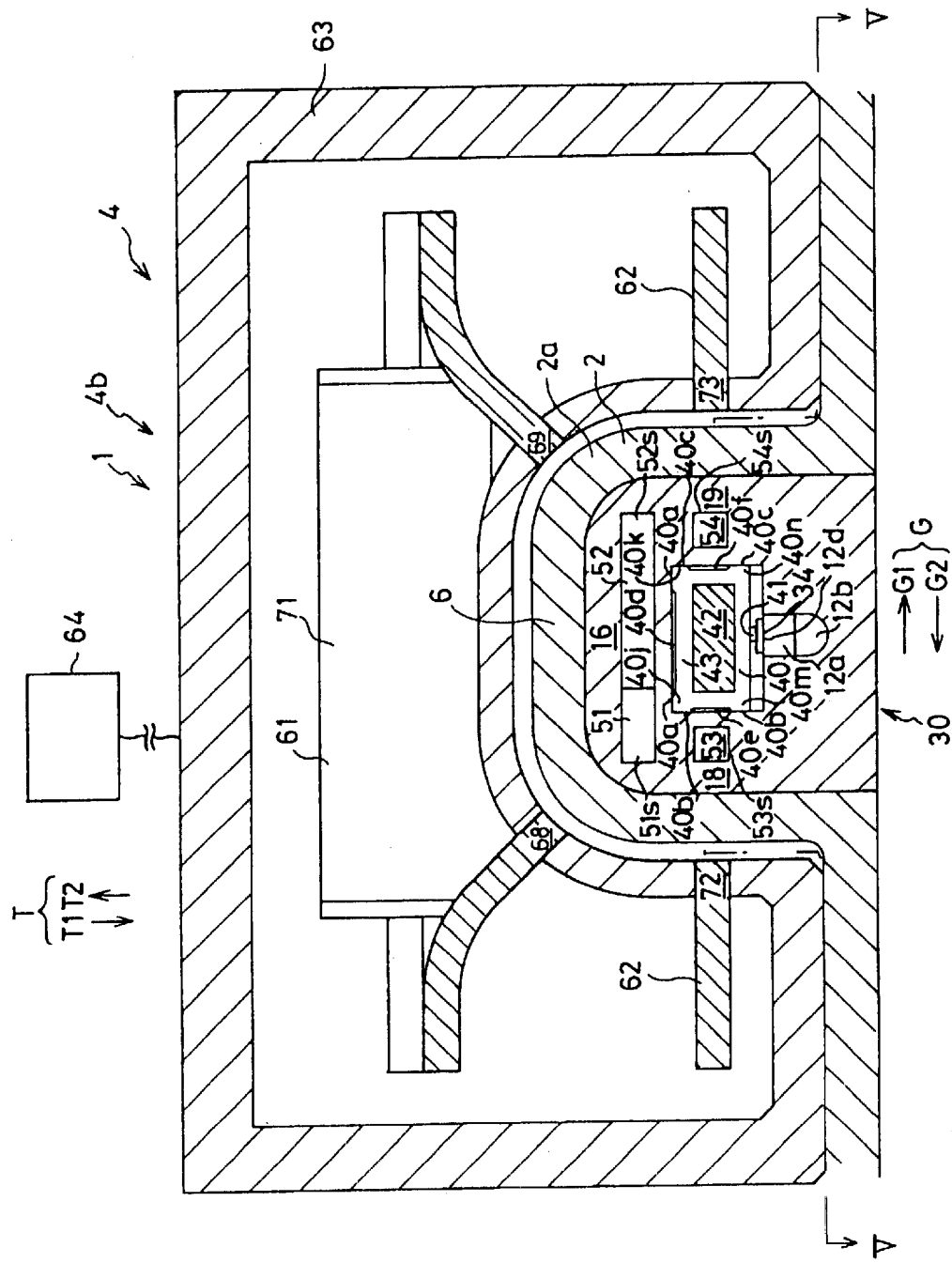
FIG. 6 is an explanatory view of a section taken along line VI—VI of FIG. 5.

As shown by FIGS. 5 and 6, the mover position controlling or set pressure controlling device 4b for controlling the position of the mover 40 of the step motor element 57 in order to control the set pressure ΔP of the valve apparatus 3, is constituted by a first and a second electromagnet 61 and 62, a control device housing 63 for accommodating the electromagnets 61 and 62 and a power feed control portion 64 (FIG. 6) feeding power to the electromagnets 61 and 62.

The control device housing 63 is provided with a recess portion 65 having a shape similar to that of the recess portion 91 of the detecting device 4a on the base 66. The first electromagnet 61 arranged in a chamber 67 of the control device housing 63, is provided with magnetic poles 68 and 69 at the positions directed to outer side end portions or contiguous end portions 51s and 52s of the stator magnetic pole pieces 51 and 52 on both sides of the eminence portion 63 when the control apparatus housing 63 is arranged at a predetermined position where the eminence position 6 is fitted to the recess portion 65 of the control device housing 63 and is provided with a coil 71 wound at a middle portion of a yoke or a magnetic core 70 connecting the magnetic poles 68 and 69. Although illustrated to enlarge for easy to see in FIGS. 5 and 6, distances between the magnetic poles 68 and 69 of the electromagnet 61 and the contiguous end portions 51s and 52s of the stator pole pieces 51 and 52 are, for example, about 1 mm in the case of the apparatus of the embodiment and the magnetic gap is extremely small. The magnetic poles 68 and 69 may be provided with widths capable of being opposed to end portions of the pole pieces such that when the magnetic poles 68 and 69 are arranged at illustrated predetermined positions, there can be applied magnetic fields for magnetizing the stator pole pieces 51 and 52 in G direction.

Similarly, the second electromagnet 62 in the chamber 67 is provided with magnetic poles 72 and 73 extended in G direction at positions directed from both sides of the eminence portion 6 to outer side end portions or the contiguous end portions 53s and 54s of the stator pole pieces 53 and 54 when the control device housing 63 is arranged and is provided with a coil 75 wound at a middle portion of a yoke 74 connecting the magnetic poles 72 and 73. Although illustrated to enlarge for easy to see in FIG. 2 or 3, distances between the magnetic poles 72 and 73 of the electromagnet 62 and the contiguous end portions 53s and 54s of the stator magnetic pieces 53 and 54 are also, for example, about 1 mm in the case of the apparatus of the embodiment. The magnetic poles 72 and 73 are provided with widths capable of being opposed to end portions of the pole pieces such that magnetic field in G direction can be applied to the stator pole pieces 53 and 54 when the magnetic poles 72 and 73 are arranged at illustrated predetermined positions. Although in the illustrated example, the widths of the magnetic pole pieces 72 and 73 are made to differ from each other, it is preferable that the widths are also to the same degree to make intensities of magnetic fields at vicinities of two magnetic pole pieces to the same degree.

Assume that in the valve system 1 having the pressure detecting and controlling device 4 including the pressure or movable position controlling device 4b constituted as described above, for example, the mover 40 of the valve apparatus 3 is under the initial state shown by FIGS. 1, 2 and 5. A state or a position of the mover 40 is specified by detecting that the above-described pattern Q is Q0, by the set pressure detecting device 4a of the pressure detecting and controlling device 4. In the case in which the electromagnets 61 and 62 are not excited by the controlling device 4b, as described above, the mover 40 under the initial state is exerted with holding force to be held at the initial position in cooperation with the stator pole pieces 53a and 54a and can be held at the position comparatively stably even when the human body 2 is applied with impact accompanied by inertia force to accelerate the human body 2 or comparatively large magnetic field in B direction or in the up and down direction T of FIGS. 1, 3 and 5. Further, with regard to a magnetic field which is uniform in G direction, even in the case in which the magnetic field is larger than a magnetic field applied on the contiguous stator pole piece by the magnet 42, in one direction inherent to the respective stable position of the mover 40, force for holding the mover 40 at the position to some degree can be exerted.

For moving the mover 40 in B1 direction, power is fed to the coil 71 of the first electromagnet 61 such that the first electromagnet 61 is excited by the power feed controller 64 in a direction by which the magnetic pole 68 of the first electromagnet 61 constitutes S pole and the magnetic pole 69 constitutes N pole in FIGS. 5 and 6. Thereby, the stator pole pieces 51a and 52a are magnetized in G2 direction and the permanent magnet 42 of the mover 40 magnetized in B1 direction, is exerted with attractive force in B1 direction by the stator pole piece 51a magnetized such that the front end side region thereof in GI direction constitutes S pole, at N pole of a front end thereof and is moved in B1 direction by E/2. Further, when the mover 40 is moved from the initial position in B1 direction even slightly, attractive force exerted to S pole of the magnet 42 of the mover 40 by N pole of an end portion in G2 direction of the stator pole piece 52a magnetized in G2 direction, is increased and the force also contributes to moving the mover 40 in B1 direction by E/2.

When the two magnetic poles of the permanent magnet 42 of the mover 40 reach positions respectively opposed to the stator pole pieces 51a and 52a, a force hampering further displacement is exerted by the two pole pieces and accordingly, the mover 40 is not moved further in B1 direction. Further, even when the excitation is stopped, magnetic poles N and S of the permanent magnet 42 are opposed to the stator pole pieces 51a and 52a and magnetize these pole pieces to thereby exert attractive force to each other and accordingly, the mover 40 is held at the position.

Next, excitation of the first electromagnet 61 is stopped and power is fed to the coil 75 of the second electromagnet 62 by the power feed controller 64 such that the second electromagnet 62 is excited in a direction by which the magnetic pole 72 of the second electromagnet 62 constitutes S pole and the magnetic pole 73 constitutes N pole. Thereby, the stator pole pieces 53a and 54a are magnetized in G2 direction and the electromagnet 42 of the mover 40 magnetized in B1 direction, is exerted with attractive force in B1 direction by the stator pole piece 53b magnetized such that a front end side region thereof in G1 direction constitutes S pole, at the front end N pole and is moved in B1 direction by E/2. Further, when the mover 40 is moved from the initial position in B1 direction even slightly, attractive force exerted to S pole of the magnet 42 of the mover 40 by N pole of an end portion in G2 direction of the stator pole piece 54a magnetized in G2 direction, is increased and the force also constitutes to moving the mover 40 in B1 direction by E/2.

Also in this case, when two magnetic poles of the permanent magnet 42 of the mover 40 reach positions opposed to the stator pole pieces 53b and 54a, a force for hampering further displacement is exerted by the two pole pieces and accordingly, the mover 40 is not further moved in B1 direction.

When desired, next, by carrying out similar power feed control except that excitation of the second electromagnet 62 is stopped and the first electromagnet 61 is excited in G1 direction, the mover 40 is further moved in B1 direction by E/2.

In accordance with movement to a state in which the mover 40 is moved from the initial state in B1 direction at intervals of pitch E/2, the projection 41 of the mover 40 reaches a position shifted from the position under the initial state in B1 direction by a distance E/2 multiplied by an integer. Therefore, the doubly supported spring 34 the end portion 32 of which is fixed and the end portion 33 of which is supported by the ball 20, is flexed downwardly and supported at a position further displaced in B1 direction. As a result, the press force exerted to the ball 20 is increased by a predetermined magnitude specified by the position and is set and controlled such that the pressure P of the cerebrospinal fluid in the upstream side cerebrospinal fluid conduit 5a is maintained at a high state by that amount. That is, after the pressure of the cerebrospinal fluid exerted to the ball 20 has been brought into a higher state, the opening 17 is opened and the cerebrospinal fluid in the upstream side cerebrospinal fluid conduit 5a is discharged to the downstream side cerebrospinal fluid conduit 5b.

As described above, according to the valve system 1, the set pressure ΔP of the valve apparatus 3 can be controlled by detecting the set pressure ΔP or a pressure set state of the valve apparatus 3 by detecting the position of the mover 40 by the set pressure detecting device 4a of the set pressure detecting and controlling apparatus 4 and changing the position of the mover 40 by the set pressure control device 4b of the set pressure detecting and controlling apparatus 4.

In the example of FIG. 1, by moving the mover 40 in B1 direction, with regard to the doubly supported spring 34, a distance between the projection 41 of the mover 40 and the end portion 33 is reduced by a unit of E/2 and a distance between the projection 41 and the end portion 32 is increased by the unit of E/2. As a result, in accordance with movement of the mover 40 in B1 direction by the unit of E/2, the press force exerted to the ball 20 by the spring 34 is increased superlinearly. In addition thereto, in the example of FIG. 1, the direction of extending the spring 34 is not in parallel with the moving direction B of the projection 41 of the mover 40. That is, the more proximate to the end portion 33 from the end portion 32, the more upward T2 the spring 34 is disposed in view of FIG. 1. Therefore, according to the example of FIG. 1, in accordance with movement of the mover 40 in B1 direction, a degree of superlinear increase of the press force exerted to the ball 20 by the spring 34 is large.

The degree of increase of the press force can previously be set and adjusted by changing a shape of an upper face 34a of the spring 34 in a state in which external force is not exerted to the spring 34, that is, in a state in which the spring 34 is not pressed by the projection 41.

More in details, at least one of thickness, width, inclination and contour line of the upper face of the spring 34 may be changed in accordance with portions of the spring 34 in B direction such that way of varying the press force of the ball 20 in accordance with movement of the projection 41 in B direction constitutes a desired pattern. In this case, the way of varying the press force may be constituted such that the press force exerted to the ball 20 by the spring 34 is increased actually linearly or increased sublinearly in accordance with movement of the mover 40 in B1 direction. Further, the degree of increase (for example, inclination in linear case) may be made comparatively large or small.

For example, with regard to the width of the spring 34, the width may be constituted such that, for example, the more proximate to the end portion 33, the larger the width, or conversely, the smaller the width, or the width may be varied along the longitudinal direction by other mode (for example, in a range from a predetermined position to the end portion 33, the more proximate to the end portion 33, the larger the width or the width is large at a central portion in B direction and small on both end sides, or the width is small at the central portion in B direction and large at the both end sides, or the width is varied periodically at pitch E/2 or at a period larger or smaller than the pitch E/2 along B direction or the like). The same goes with the thickness and the thickness may be varied along the longitudinal direction instead of or along with varying the width of the spring 34 or the thickness may be varied in the above-described mode. A total of the thickness in the width direction may be varied or a portion of the thickness in the width direction may be varied such that a projected shape or a recess groove extended in a desired range along the longitudinal direction is provided. Further, the spring 34 may be fabricated such that while the thickness stays substantially in a constant state, in view of a cross-sectional face orthogonal to the longitudinal direction, a recess portion is formed at one face and a projected portion is formed at other surface. With regard to the inclination, in the case in which the spring 34 is formed in a flat plate shape, a relative height between the end portion 32 and 33 in FIG. 1 is changed and the spring 34 may be extended in a direction actually in parallel with the B direction or may be inclined slightly in a direction counter to that in the case of FIG. 1. The change of the inclination of the spring in the flat plate shape becomes change of contour of the upper face of the spring. Meanwhile, the contour of the upper face may be changed by changing the thickness of the spring. The above-described change increases or reduces a spring constant K with regard to flexing or bending deformation of the spring 34 in C direction and changes a way of varying the spring constant K depending on the fulcrum position D of the spring 34.

Figure 7:
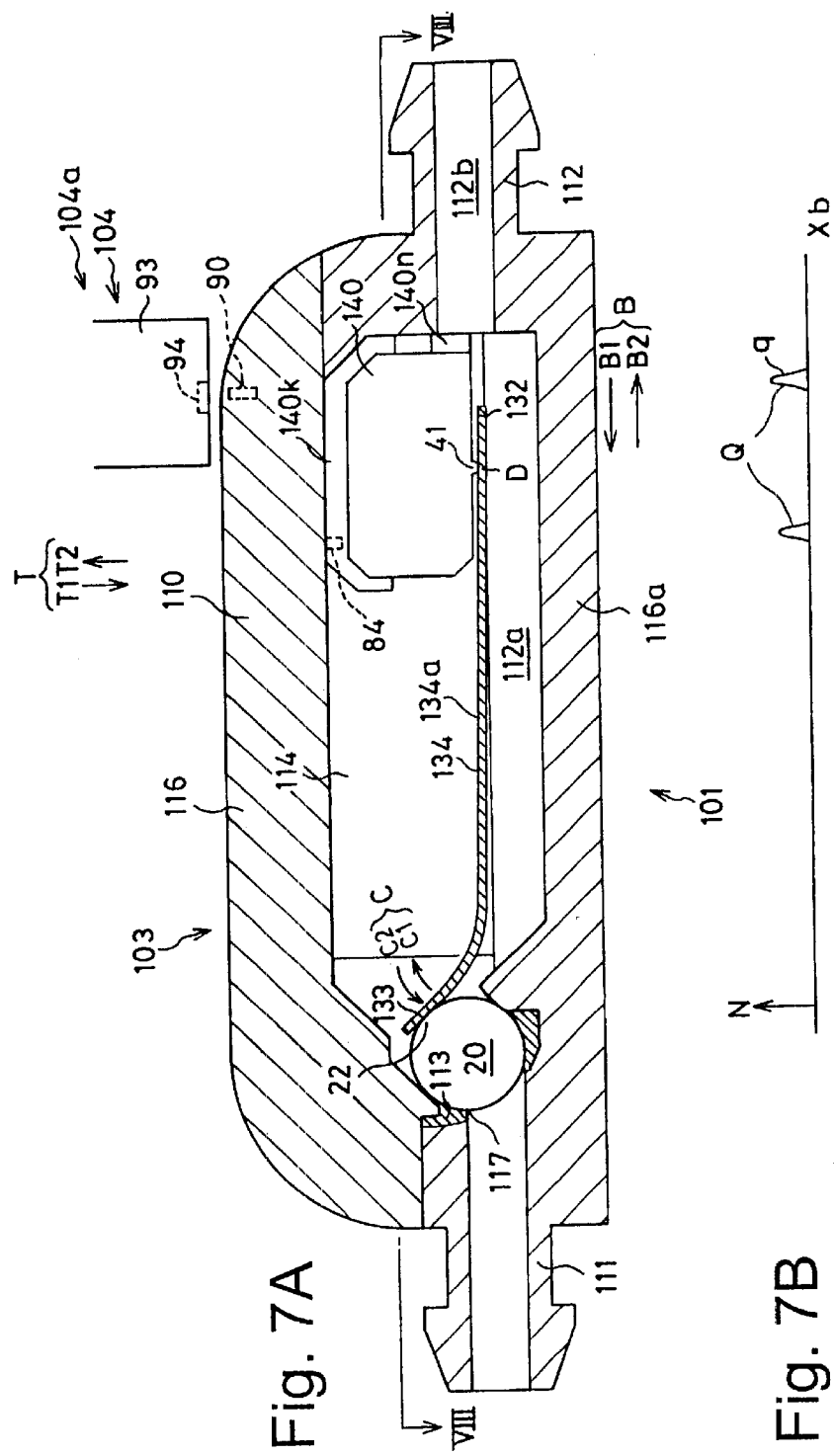
FIG. 7 are for explaining a valve system of other preferable embodiment according to the invention in which FIG.

Next, an explanation will be given of a valve system 101 according to other embodiment in reference to FIGS. 7 and 8. In the valve system 101, elements, members and portions the same as or similar to those in the valve system 1 are attached with the same notations and actually corresponding elements, members and portions are attached with notations added with 1 at first portions thereof.

The valve apparatus 103 of the valve system 101 grossly differs from the valve system 1 in that in place of the linear step motor element 57 as the step motor element, there is used a rotary step motor element 157 having a rotor 80 and the rotary step motor element is coupled to the mover 140 which is reciprocally movable linearly in B direction via a motional direction converting mechanism 81, that the movable magnetic marker 84 is embedded in the movable member 140, that a spring 134 is not formed in a flat plate shape but is bent at a vicinity of an end portion 133 and an upper face (surface disposed on upper side in view of FIG. 7) 134a of the spring 134 is extended substantially in parallel with B direction at a central portion of the spring 134 in the longitudinal direction, and that a bottom portion of a second conduit portion 112b in an outlet side conduit portion 112, is disposed above a bottom portion of a first conduit portion 112a. Further, the first conduit portion 112a is in a mode of a groove extended in B direction at an upper face of a bottom wall 116a of a valve housing 110 and an upper portion thereof is opened to a chamber 114 of the valve housing 110. Further, a valve apparatus 103 of the valve system 101 is similar to the valve apparatus 3 of FIG. 1 in that the chamber 114 constitutes a portion of a flow path in cooperation with the conduit portion 112a.

Figure 8:
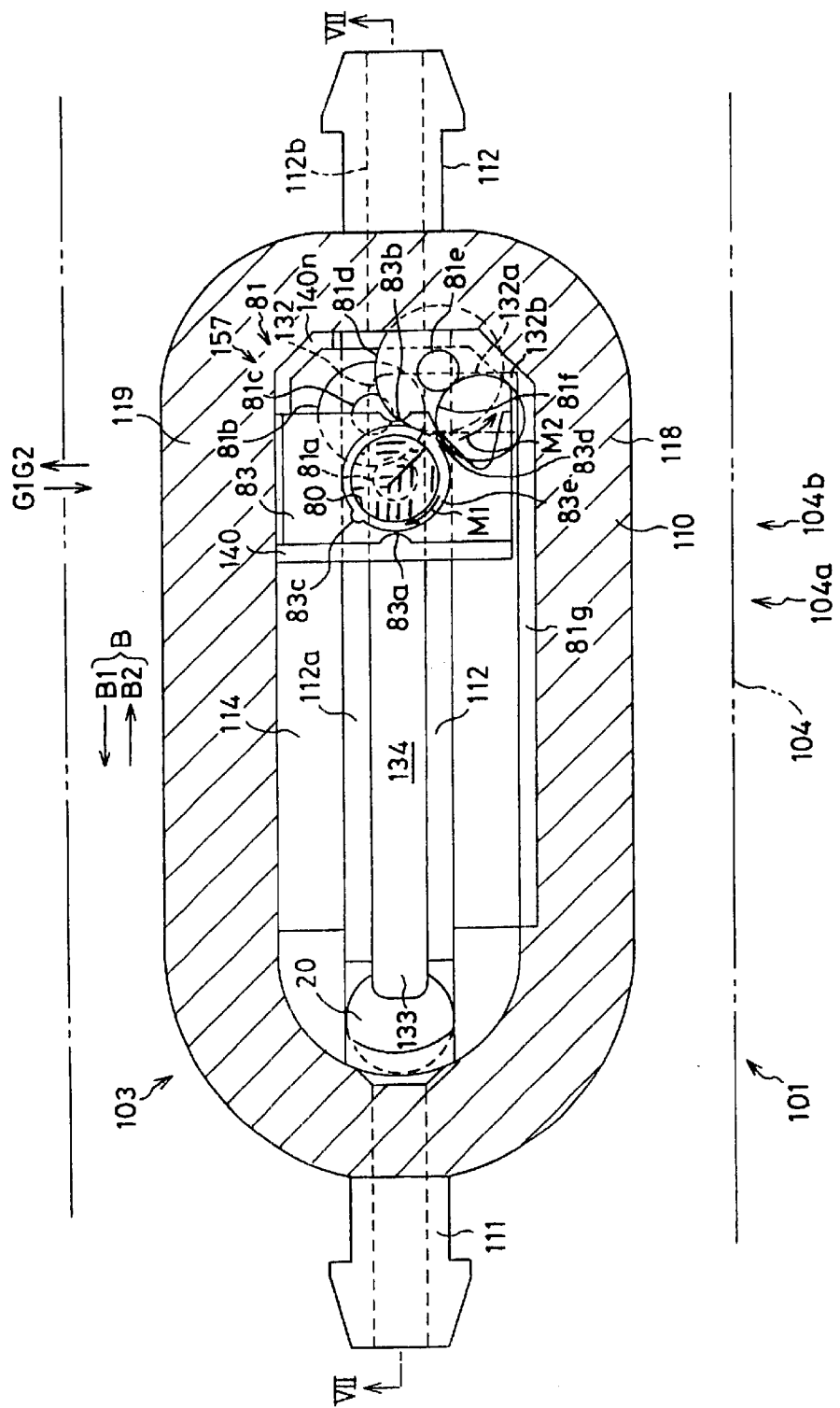
FIG. 8 is an explanatory view of a section taken along a line VIII—VIII of the valve system of FIG. 7.

More in details, as is apparent from FIG. 8, according to the spring 134 of the valve apparatus 103 of the valve system 101, a base end portion 132 is provided with an arm portion 132a bent in an L-like shape and is fixed to a side wall 118 of a housing 110 at an extended end 132b of the arm portion 132a and the spring 134 is pushed to the upper portion 22 of the ball 20 in C2 direction (FIG. 7) at the other end or front end 133 and is pressed by the projection 41 of a slider 140 at the middle movable fulcrum position D. The base end portion 132 may be provided with a mode of a head portion of "T" as in the valve system 1 of FIG. 1 instead of the arm portion in the L-like shape.

The step motor element 157 is typically provided with the rotor 80 in a shape of a circular disk comprising a permanent magnet magnetized in the diameter direction, and a stator 83 having outer notches 83a and 83b for forming magnetically saturated portions at outer side edges thereof and inner notches 83c and 83d specifying a static stable position of the rotor 80 in a direction shifted by 90 degree on a peripheral face of a rotor containing hole 83e and comprising a soft magnetic material having high permeability in a structure known as a step motor for an electronic type analog wrist watch.

According to the step motor element 157, in a state in which the stator 83 is not magnetized, magnetostatic holding force of the rotor 80 is maximized when magnetic poles N and S at both ends in the diameter direction are opposed to peripheral face portions of the hole 83e of the stator 83 where the inner notches 83c and 83d are not present and is held stably at a position where a direction of magnetizing the rotor 80 is directed in a direction orthogonal to a direction connecting the inner notches 83c and 83d. Therefore, even when the human body is vehemently moved and impact force or inertia force is exerted, not only a rotational position of the rotor 80 is difficult to vary but also the rotor 80 is restored to an original position with regard to rotation less than quarter rotation. Meanwhile, when a pulse-like magnetic field having comparatively gradual rise is applied to the stator 83 in a direction (G1 or G2) for moving the rotor 80 disposed at a statically stable position in a direction M1 for moving magnetic poles of the rotor 80 to the outer notches, the rotor 80 is rotated in the M1 direction and reaches a static stable position having a direction different by 180 degree. When the stator 83 is alternately magnetized periodically in G1 direction and G2 direction, the rotor 80 is rotated in M1 direction.

The step motor element 157 may be an element of a step motor of other kind so far as a rotor can be held at a rotational position when a stator is not magnetized by outside magnetic field.

The motional direction converting mechanism 81 is provided with a rotation output gear 81a coaxially formed at an output shaft 80a integral with the rotor 80, a first gear 81b in mesh with the gear 81a, a first pinion 81c coaxial with the gear 81b, a second gear 81d in mesh with the pinion 81c, a second pinion 81e coaxial with the gear 81d, a pinion gear 81f in mesh with the pinion 81e and a rack 81g having rack teeth in mesh with the pinion 81f and extended in B direction.

According to the motional direction converting mechanism 81, rotation of the rotor 80 is decelerated by mesh of the gears 81a and 81b, the gears 81c and 81d and the gears 81e and 81f and accordingly, at every half rotation of the rotor 80 in the clockwise direction M1 in FIG. 5, the pinion 81f is rotated by a very small angle in the counterclockwise direction M2 and the movable member 140 is moved by a very small amount in B1 direction by being guided by the rack teeth 81g. Further, a number of the gears may be smaller or larger.

Further, in order to rotate the rotor 80 in M2 direction in the step motor element 157 in order to move the movable member 140 in B2 direction, as is known as way of operational control of the motor element 157 of this kind in the field of the electronic type analog timepiece, the rotor is pivoted around a stationary state stabilizing position by a pulse-like magnetic field having small intensity and width and when a direction of magnetizing the rotor 80 exceeds a direction in parallel with G direction and the rotor is pivoted in the reverse direction M2, comparatively large pulse-like magnetic field is applied and the rotor 80 may be rotated in the reverse direction M2 as it is.

Further, in the case in which a failsafe direction of moving the movable member 140 is B2 direction (case of application object in which failsafe operation is directed in a direction of reducing set pressure), positions of the inner notches may be provided on opposite sides and in a normal alternating pulse, the movable member 140 may be moved in B2 direction.

Similar to the movable member 40 of FIG. 1, the movable member 140 is provided with projected portions such as projected portions 140k and 140n at corner portions such that the movable member 140 can be brought into sliding contact with the wall portion 116 or the like of the valve main body 110 at the corner portions and a flow path is formed between the projected portion.

The fixed magnetic marker 90 is embedded in the top wall 116 at a vicinity proximate to one edge portion (vicinity of end portion in G2 direction) in the width direction of the top wall 116 within the range of the width of the chamber 114 of the main body 110 and the movable magnetic marker 84 is embedded in the mover 140 at a position the same as that of the fixed magnetic marker 90 with regard to the width direction G. In this case, as explained in reference to FIGS. 1 through 3, the magnetic sensor 94 is arranged also at a position where the magnetic sensor 94 can pass through just above both of the fixed magnetic marker 90 and movable magnetic marker 84 when the detector slider 93 is slid in B direction in a state in which the main body portion 92 of the set pressure detecting device 4b is arranged at the predetermined position. Although other structure of the pressure detecting device 104a cannot be illustrated in FIGS. 7 and 8, the structure is similar to that in the case of FIGS. 1 through 3.

Also in the case of the pressure detecting device 104a, as shown in FIG. 7B, similar to the case of the example of FIG. 4, the position of the fixed magnetic marker 90 and the position of the movable magnetic marker 84 can be detected from peak positions of the detection output Q of the intensity of the magnetic field detected by the sensor 94 by scanning or moving the magnetic sensor 94 in B direction via the detector slider 93 and the press force exerted to the end portion 133 of the spring 134 or the set pressure ΔP applied on the ball 20 can be detected by detecting the position of the mover 140, that is, the position of the fulcrum projection 41 from magnitude of positional deviation in B direction of the movable magnetic marker 84 relative to the fixed magnetic marker 90. In the case of this example, although a stable position in B direction which can be taken by the mover 140 is substantially continuous, different from the case of the valve apparatus 3, there is no magnetic member such as the stator pole piece in the top wall 116 of the main body 110 and therefore, there is less concern of disturbing the magnetic field formed by the magnetic markers 90 and 84 by the main body 110 and accordingly, the positions of the two markers 90 and 84 are easy to specify accurately.

Positions of attaching the markers 90 and 84 and the magnetic sensor 84 may be at different positions such as, for example, central portion in the width direction G so far as the magnetic sensor 94 can linearly pass through locations as proximate to the markers 90 and 84 as possible such that the magnetic sensor 94 can firmly detect the magnetic fields formed by the markers 90 and 84 to there by enable to specify the positions of the markers 90 and 84. Further, when desired, the markers 90 and 84 may be arranged different positions with regard to the width direction, the magnetic sensor 84 may be scanned in B direction (longitudinal direction) while making the magnetic sensor 84 execute line scanning in G direction (transverse direction) and a face area may be scanned by the magnetic sensor 84 as a whole. Although in the illustrated example, the movable magnetic marker 84 is formed at the vicinity of the end portion in B1 direction of the mover 140 to minimize concern that the magnetic field formed by the magnetic marker 84 comprising the permanent magnet is disturbed by the stator 83 or the rotor magnet 80, depending on cases, the movable magnetic marker 84 may be disposed at a position further proximate to the stator 83 or the rotor 80 or a position overlapping these with regard to the up and down direction T of FIG. 7 since in detecting position by the magnetic sensor 94, the rotor 80 is stopped, the magnetic fields formed by the rotor 80 and the stator 83 constitute static magnetic fields which are constant over time and accordingly, the influence or noise is easy to separate.

According to the valve system 101, constituted as described above, the mover 140 can be moved in B1 direction or B2 direction by respective very small distance by mounting the pressure controlling device 104b having the electromagnets similar to the electromagnet 62 at the predetermined position around the eminence portion embedded with the main body 110 similar to the case of the pressure controlling device 4b of FIGS. 5 and 6 and applying the predetermined pulse-like magnetic field in G direction to the stator 83 of the motor element 157 by the electromagnets.

Further, the electromagnets similar to the electromagnet 62 are provided with shape or arrangement of magnetic poles capable of applying the pulse magnetic field in G direction over an entire range in B direction by which the stator 81 of the movable member 140 can be moved. A number of slender soft magnetic material pieces having high permeability may be embedded to the side walls 118 and 119 of the main body 110 similar to the stator pieces 53 and 54 in order to increase the intensity of the magnetic field applied to the stator 83 by the pressure adjusting and controlling device 104 and to enhance orientation of the magnetic field in G direction.

When the movable member 140 is moved in B1 direction, the position D of the fulcrum pushed by the projection 41 of the movable member 140 is also moved in B1 direction and therefore, the C2 direction press force exerted to the ball 20 by the end portion 133 of the spring 134 is increased and the pressure of the tube path 111 on the upstream side of the opening 117 of the ball valve is adjusted to a high state. Similarly, movement of the valve member 140 in B2 direction constitutes an adjustment in a direction of reducing the adjusted pressure.

Therefore, also according to the valve system 101, the set pressure ΔP of the valve apparatus 103 can be controlled by detecting the set pressure ΔP or the pressure set state of the valve apparatus 103 by detecting the position of the mover 140 by the set pressure detecting device 104a of the set pressure detecting and controlling apparatus 104 and changing the position of the mover 140 by the set pressure controlling device 104b of the set pressure detecting and controlling apparatus 104.

Next, an explanation will be given of an example of a valve system 201 having a set pressure variable valve apparatus 203 having a rotor comprising a multiple poles permanent magnet structure as shown by Japanese Patent Laid-Open No. 40063/1985. In the valve system 201, elements, members or portions the same as or similar to those in the valve system 1 are attached with the same notations and actually corresponding elements, members the portions are attached with notations added with 2 at first portions.

The valve apparatus 203 is provided with a rotor 240 as a mover comprising a multiple poles permanent magnet structure having a plurality (for example, 8) of permanent magnet portions magnetized in reverse directions in view from the axial direction T alternately at equal intervals along the peripheral direction. A central portion 240*a* of the rotor 240 is integrally formed with a cam 241 having multiple stages of cam faces 241*a* in a shape of a spiral staircase in correspondence with magnetic poles of the permanent magnet. A spring 234 is arranged between the cam 241 and the valve element 20 in a ball-like shape. The spring 234 is formed in a fork-like shape having, for example, three of leg portions or arm portions 234*a*, 234*b* and 234*c*, locked by a support structure 216*b* fixed to a bottom wall 216*a* of a main body 210 by front ends of the short arm portions 234*b* and 234*c* on both sides, brought into contact with the ball 20 by a front end 233 of the long arm portion 234*a* at the center and is brought into contact with the cam face 241*a* of the cam 241 in the spiral shape at a base end portion 232 of the fork disposed at the base end portion of the arm portion 234*a*. Therefore, when the rotor 240 is rotated around a central axis line, the base end portion 232 of the spring 234 is moved in the axial direction T by the cam 241 to thereby change the flexing state of the spring 234, change the press force in C2 direction exerted to the ball 20 by the end portion 233 of the spring 234 and change pressure which the ball 20 releases closure of a valve flow path 217. A projection 232*a* of the arm base end portion 232 is brought into a stable state by being engaged with any of the cam faces 241 in the shape of the spiral staircase and accordingly, the rotor 240 takes a rotational position rotated by a predetermined angular pitch.

The valve apparatus 203 is further provided with a fixed magnetic marker 290 embedded in a top wall 216 of the main body 210 and a movable magnetic marker 284 mounted to an upper portion of an outer peripheral region 240*b* of the rotor 240. The fixed magnetic marker 290 and the movable magnetic marker 284 are respectively constituted by, for example, permanent magnets and the movable magnetic marker 284 is coated with silicone resin which is inactive to physical fluid or the like when desired. In view of a plane sectional view of FIG. 9A, for example, as illustrated by imaginary lines in the drawing, the fixed magnetic marker 290 is embedded in the top wall 216 at a location proximate to the outer periphery of the rotor 240 and disposed on the outer side in the radius direction of the movable magnetic marker 284. However, when desired, in view by a plane view, the fixed magnetic marker 290 may be disposed on the inner side in the radius direction of a path of moving the movable magnetic marker 284 and the fixed magnetic maker 290 may be disposed on the path of moving the movable magnetic marker 284 when intensity of magnetic field is detected and identified.

Similar to, for example, the detecting device main body 92 of FIGS. 1 through 3, a set pressure detecting device 204*a* of a pressure detecting and controlling apparatus 204, is provided with a detecting device main body 292 constituted to be able to position and arrange relative to the eminence portion 6 of a portion of embedding the valve apparatus 203, a rotating plate 293 rotatably supported by the detecting device main body 292 and a magnetic sensor 294 mounted to a lower face of the rotating plate 293 in view from FIG. 9B.

In this case, a pattern shown by FIG. 9C is displayed by a display 296 by detecting a rotational position of the rotating plate 293 relative to the main body 292 by a rotational angle sensor 295 while rotating the rotating plate 293 and transmitting the rotational position to the display 296 and transmitting detection output N of magnetic field by the magnetic sensor 294 to the display 296, there is calculated a magnitude of a deviation in angle Ra in the rotational direction R (rotational angle) between a peak of a pattern "q" of intensity of a magnetic field caused by the fixed magnetic marker 290 and a peak of a pattern "Qv" of intensity of a magnetic field caused by the movable magnetic marker 284, and based on the magnitude of the deviation, the rotational position of the cam 241 of the rotor 240 may be calculated and the set pressure ΔP of the valve apparatus 203 may be calculated.

Further, when a rotational center Rd of the rotating plate 293 is difficult to position to align easily to a rotational center Rr of the rotor 240 since the shape of the eminence portion 6 embedded with the valve apparatus 203 is difficult to be constant, it is preferable that sizes in B direction and G direction of a recess portion 291 of the detecting valve main body 292 similar to the recess portion 91 of the detecting apparatus main body 92, is made slightly larger than that of the eminence portion 6 such that the detecting device main body 292 can adjust the position. In such a case, for example, as shown by imaginary lines in FIG. 9B, another fixed magnetic marker 290*a* which can be regarded to mount substantially stationally to the main body 210, is provided at the top portion of the rotational center Rr and another magnet sensor 294*a* is provided at the rotational center Rd of the rotating plate 293, the detecting device main body 292 is mounted onto the eminence portion and positionally shifted in B direction and G direction to thereby find a location where detection output of the fixed magnetic marker 294*a* by the magnetic sensor 290*a* is maximized by which the detecting device main body 292 may previously be positioned relative to the valve apparatus 203.

Further, change and control of the set pressure ΔP of the valve apparatus 203 detected in this way are similar to those in normal rotational position control of a rotary type step motor having a rotor comprising a multiple poles permanent magnet structure and the stator structure having desired structure may be arranged at a predetermined position of the surface of the skin to thereby change and control the rotational position of the rotor. As such a stator structure, for example, a constitution explained by notation 390 as a valve adjusting element in Japanese Patent Laid-Open No. 40063/1985, can be used.

What is claimed is:

1. A pressure variable valve apparatus which is configured to be embedded in a living body and having a variable set pressure, the pressure variable valve apparatus comprising:
    a housing defining a fluid flow path;
    a valve element disposed in the housing for releasably closing the fluid flow path;
    a movable member linearly movable in the housing to change a pressure in the fluid flow path by varying the closure of the fluid flow path by the valve element;
    a fixed magnetic marker mounted stationary to the housing; and
    a movable magnetic marker integrally formed with the movable member.

2. A valve apparatus according to claim 1; further comprising a linear step motor, the movable member comprising a linearly driven element of the linear step motor.

3. A valve apparatus according to claim 2; wherein the linearly driven element includes a permanent magnet, and the movable magnetic marker comprises the permanent magnet of the linearly driven element.

4. A valve apparatus according to claim 1; further comprising a rotary step motor, and a converting mechanism for converting rotation of a rotor of the rotary step motor into a linear motion, the linearly driven element being coupled to the converting mechanism.

5. A valve apparatus according to claim 1; wherein the valve apparatus is configured to be mounted in the living body to adjust a pressure of a fluid in the living body.

6. A valve apparatus according to claim 1; further comprising a set pressure detecting apparatus mounted to the housing for detecting a set pressure of the valve apparatus.

7. A valve apparatus according to claim 6; wherein the set pressure detecting apparatus comprises a magnetic sensor, and a supporter for movably supporting the magnetic sensor outside of the living body so that the magnetic sensor provides an indication of relative positions of the fixed magnetic marker and the movable magnetic marker.

8. A valve apparatus according to claim 6; wherein the set pressure detecting apparatus comprises a magnetic sensor, and a supporter for movably supporting the magnetic sensor outside of the living body so that the magnetic sensor is movable in a direction of movement of the movable magnetic and provides an indication of relative positions of the fixed magnetic marker and the movable magnetic marker.

9. A valve apparatus according to claim 1; further comprising an elongate elastic member having a fixed base end portion and a front end portion of which is urged by the movable member into contact with the valve element, the movable element being linearly movable along a longitudinal direction of the elongate elastic member between both end portions thereof and having a fulcrum portion for flexing the elastic member between the both end portions.

10. A variable pressure valve apparatus according to claim 9; wherein the elongate spring member comprises a leaf spring.

11. A variable pressure valve apparatus according to claim 10; wherein the leaf spring has a first end portion disposed in pressure contact with the valve element and a second end portion in contact with the movable member.

12. A valve apparatus according to claim 1; wherein the valve apparatus is configured to be mounted in the living body to adjust a pressure of the cerebrospinal fluid in the living body.

13. A valve apparatus according to claim 1; wherein the movable member includes a magnet; and further comprising position control device disposed in the housing for applying a magnetic field to move the movable member to control a pressure in the fluid flow path by varying the closure of the fluid flow path by the valve element.

14. A variable pressure valve apparatus comprising: a housing defining a fluid conduit having a fluid inlet port and a fluid discharge port; a valve element for releasably closing one of the fluid inlet and outlet ports; an elongate spring member disposed in the housing for biasing the valve element in a closing direction to control a flow pressure of a fluid; a movable member linearly slidable relative to the elongate spring member and in contact therewith for controlling a biasing force of the spring member on the valve element; and a driving mechanism for driving the movable member to slide relative to the elongate spring member to control the fluid pressure.

15. A valve according to claim 14; wherein the valve element comprises a ball for releasably closing a valve seat formed in the fluid conduit.

16. A valve according to claim 15; wherein the elongate spring member has a first end fixed in the housing and a second end opposite the first end in contact with the valve element.

17. A valve according to claim 14; wherein the movable member comprises a magnetic member, and the driving mechanism comprises a series of magnets disposed in the housing along the length of the elongate spring member for selectively moving the moving member along the slidable path by applying a magnetic field thereto.

18. A valve according to claim 14; wherein the driving mechanism comprises a rotary step motor and a converting mechanism for converting rotary motion of the motor into linear motion of the movable member.

19. A valve according to claim 14; further comprising a magnetic marker mounted stationary in the housing, a movable magnet mounted to undergo movement with the movable member, and a magnetic sensor for sensing relative positions of the magnetic marker and the movable magnet for providing an indication of a pressure.

20. A pressure variable valve apparatus which is configured to be embedded in a living body and having a variable set pressure, the pressure variable valve apparatus comprising:

a housing defining a fluid flow path;

a valve element disposed in the housing for releasably closing the fluid flow path;

a rotary type step motor element disposed in the housing and having a rotor comprising a multiple pole permanent magnet structure, a rotational position of the rotor being adjustable to change a pressure of the fluid by varying the closure of the fluid flow path by the valve element; and a fixed magnetic marker integrally formed with the rotor.

* * * * *